United States Patent
Verdonk et al.

(10) Patent No.: US 6,642,498 B2
(45) Date of Patent: Nov. 4, 2003

(54) MICROMIRROR OPTICAL MULTIPLEXER AND METHOD FOR DIRECTING LIGHT TOWARDS AN ARRAY OF SENSORS

(75) Inventors: Edward Verdonk, San Jose, CA (US); David A. King, Menlo Park, CA (US); Richard D. Pering, Mountain View, CA (US); Richard J. Pittaro, San Carlos, CA (US); Shahida Rana, Fremont, CA (US); Frederick A. Stawitcke, Sunnyvale, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 105 days.

(21) Appl. No.: 09/990,609

(22) Filed: Nov. 21, 2001

(65) Prior Publication Data

US 2003/0094564 A1 May 22, 2003

(51) Int. Cl.[7] .............................. G01J 1/42; H01J 3/14; G02B 6/26
(52) U.S. Cl. ....................... 250/208.2; 250/234; 385/18; 359/128
(58) Field of Search ........................... 250/201.1, 201.9, 250/208.2, 234, 458.1, 459.1, 461.1, 461.2; 385/16–18, 24; 359/115, 124, 128

(56) References Cited

U.S. PATENT DOCUMENTS

| 4,657,736 A | 4/1987 | Marsoner et al. ............. 422/56 |
| 4,892,640 A | 1/1990 | Wolfbeis et al. ............. 204/418 |
| 5,061,049 A | 10/1991 | Hornbeck ..................... 359/224 |
| 5,340,722 A | 8/1994 | Wolfbeis et al. .............. 435/14 |
| 5,372,936 A | 12/1994 | Fraatz et al. ................... 435/34 |
| 6,396,053 B1 * | 5/2002 | Yokoi |
| 6,396,976 B1 * | 5/2002 | Little et al. |
| 6,427,038 B1 * | 7/2002 | Britz et al. |
| 2002/0154851 A1 * | 10/2002 | Yet et al. |
| 2003/0012487 A1 * | 1/2003 | Hamerly et al. |

* cited by examiner

*Primary Examiner*—David Porta
*Assistant Examiner*—David C. Meyer (57) ABSTRACT

The present invention is directed to a micromirror optical multiplexer for directing light to an array of sensors. The micromirror optical multiplexer directs light from one or more sources onto multiple, coplanar sensors for the purpose of exciting fluorescence. The micromirror optical multiplexer includes at least one light source and a micromirror array having a top face and up to four side faces. Pivotable mirrors of the micromirror array are arranged in a multiple row, multiple column format on the top face. In addition, each of the side faces of the micromirror array has at least one row of pivotable mirrors. By pivoting one side face mirror and one top face mirror, a light source entering at one corner of the micromirror array can be directed to exit near normal incidence anywhere on the bottom of the device.

26 Claims, 6 Drawing Sheets

MICROMIRROR OPTICAL MULTIPLEXER AND METHOD FOR DIRECTING LIGHT TOWARDS AN ARRAY OF SENSORS

BACKGROUND OF THE INVENTION

1. Technical Field of the Invention

The present invention relates generally to sensor arrays, and specifically to optical multiplexers for directing light toward the sensor arrays.

2. Description of Related Art

Biochemical sensors based on fluorescence are used for many different types of analytes of physiologic interest. For example, fluorescence-based blood analyzers that measure blood gases, electrolytes, metabolites, coagulation state and immunological markers are commercially available. The ability to measure multiple analytes in parallel is generally useful for the diagnosis of a patient's state of health. To measure multiple analytes in parallel requires an array of biochemical sensors and an optical device to excite and read the array.

Current optical devices measuring fewer than ten biochemical sensors often have a dedicated optical source for each sensor. As the number of biochemical sensors increases, it becomes advantageous to share device hardware, especially illumination hardware, for multiple sensors. The ability to share illumination hardware is especially important when the optical device is a small, handheld device.

One possible solution involves translating the biochemical sensors on a mechanical stage. However, this approach is overly complicated and expensive for a small, handheld optical device. Alternatively, the light source can be directed or steered using either a single moving mirror, or a micromirror array, as described in U.S. Pat. No. 5,061,049, which is hereby incorporated by reference. However, existing moving mirror devices require a large spatial separation between the mirror and the sensor plane, which increases the thickness of such devices beyond what is feasible for a small, handheld optical device.

SUMMARY OF THE INVENTION

The present invention is directed to a micromirror array for use within an optical multiplexer. The micromirror array includes a top face and at least one side face. Pivotable micromirrors of the micromirror array are arranged in a multiple row, multiple column format on the top face. In addition, each of the side faces of the micromirror array has at least one row of pivotable micromirrors. In operation, a first micromirror on one of the side faces of the micromirror array is capable of redirecting light propagating substantially parallel to the side face towards the top face. A second micromirror on the top face redirects the light propagating parallel to the top face to exit the micromirror array.

In one embodiment, the optical multiplexer including the micromirror array steers light from a single source onto multiple, coplanar sensors for the purpose of exciting fluorescence. Thus, by pivoting one side face micromirror and one top face micromirror, a light source entering at one corner of the micromirror array can be directed to exit near normal incidence anywhere on the bottom of the device. In other embodiments, this approach can be extended to direct light from more than one source. For example, as many as eight sources, two per corner, can be directed (provided that the side face micromirrors pivoted ±45° about their vertical centerlines and the top face micromirrors pivoted above ±45° about their two orthogonal centerlines).

The micromirror optical multiplexer can be implemented within a small, handheld optical device capable of reading fluorescence from multiple biochemical sensors. Advantageously, the small, handheld optical device can be made compact with a flat form factor (i.e., <10 mm thick). Moreover, when making fluorescence measurements on a sample of blood, it is preferred that neither the excitation nor the emission light pass through the blood to avoid known autofluorescence of certain plasma proteins and scattering from the red blood cells. Therefore, the micromirrors of the top face of the micromirror array are preferably dichroic mirrors, which allow the illumination of a biochemical sensor with excitation light and the collection of the resultant fluorescent light from the same side of the sensor.

BRIEF DESCRIPTION OF THE DRAWINGS

The disclosed invention will be described with reference to the accompanying drawings, which show important sample embodiments of the invention and which are incorporated in the specification hereof by reference, wherein.

DETAILED DESCRIPTION OF THE EXEMPLARY EMBODIMENTS OF THE INVENTION

The numerous innovative teachings of the present application will be described with particular reference to exemplary embodiments. However, it should be understood that these embodiments provide only a few examples of the many advantageous uses of the innovative teachings herein. In general, statements made in the specification of the present application do not necessarily delimit any of the various claimed inventions. Moreover, some statements may apply to some inventive features, but not to others.

Figure 1:
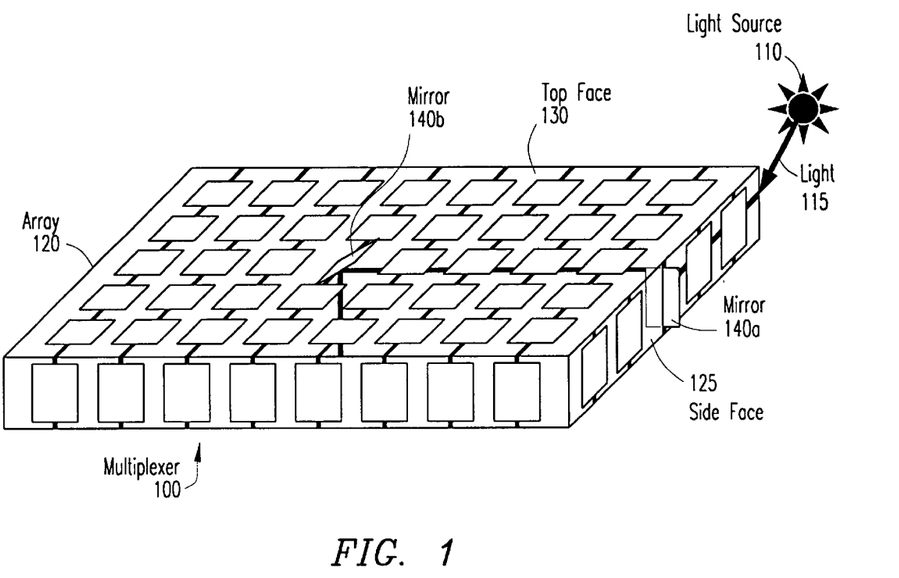
FIG. 1 is a plan view of an exemplary micromirror optical multiplexer in accordance with embodiments of the present invention.

FIG. 1 shows a plan view of a preferred embodiment of a micromirror optical multiplexer 100 in accordance with embodiments of the present invention. The micromirror optical multiplexer 100 includes at least one light source 110 and a micromirror array 120. The array 120 has a top face 130 and up to four side faces 125. As can be seen in FIG. 1, the micromirror array 120 resembles a removable lid to a box having no bottom face. However, it should be understood that the present invention extends to embodiments where the micromirror array 120 has a bottom face capable of transmitting light. On the top face 130 of the array, the micromirrors 140 are arranged in a multiple row, multiple column format. On each of the side faces 125, there is at least one row of micromirrors 140.

Each of the micromirrors 140 of the array 120 is capable of being pivoted along at least one axis of the micromirror 140. In one embodiment, the axes include at least one centerline. A centerline extends between two opposite sides of the micromirror 140, and divides the micromirror in half, such that the areas on either side of the centerline are substantially equal. In other embodiments, the axes may include any axis of the micromirrors 140. For example, one of the axes may be an edge of the micromirrors 140, thereby increasing the effective reflective area of the micromirror 140. However, it should be noted that if the axes are not axes of symmetry (i.e., centerlines), the micromirrors 140 may only be able to reflect incident light from one direction, rather than two opposing directions, as is possible with centerline pivoting.

FIG. 1 illustrates a 1:40 micromirror optical multiplexer 100, in which the multiplexer 100 takes light 115 from a single source 110 and directs that light 115 to exit at one of forty locations in a plane at the bottom of the top face 130 of the device 100 by pivoting one of the side face mirrors 140a and one of the top face mirrors 140b. It should be understood that the multiplexer 100 may include greater or fewer number of exit points, depending on the number of sensors that the multiplexer 100 transmits light to. In addition, it should be understood that the top face 130 of the device 100 should be large enough to cover the associated array of sensors. For example, the multiplexer 100 may be 15 mm×15 mm on the top face 130, and the side faces 125 may be approximately 1 mm high.

Figure 2:
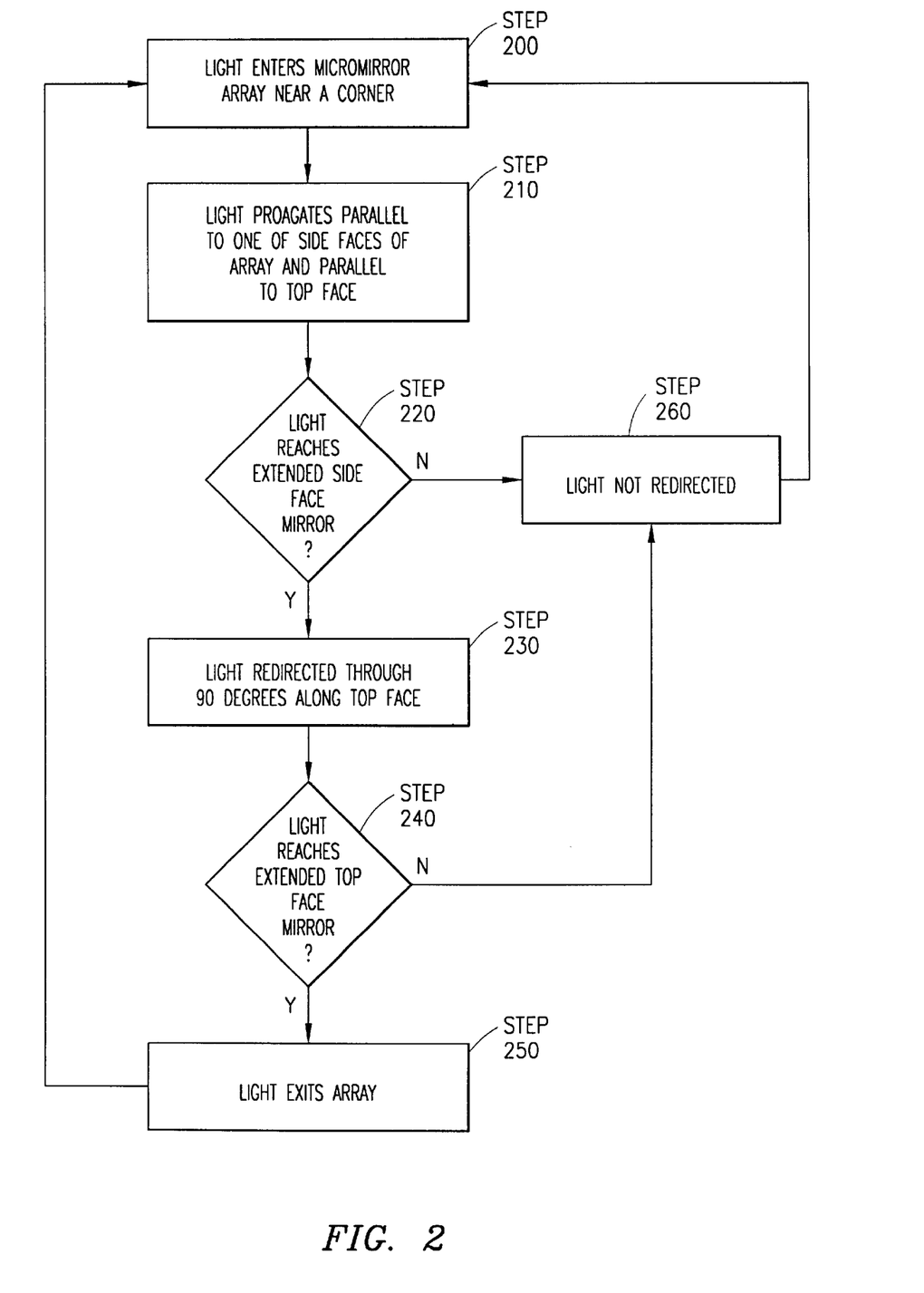
FIG. 2 is a flow chart illustrating the steps for directing light using the exemplary micromirror optical multiplexer shown in FIG. 1.

In operation, as illustrated in the steps of FIG. 2, collimated light from the light source enters the micromirror array near one of the corners (step 200) and propagates substantially parallel to one of the side faces (step 210) until the light reaches one of the micromirrors along that side face (step 220) that is extended to redirect the light, through 90°, along the top face (step 230). The light travels substantially parallel to the top face until the light reaches a second micromirror on the top face (step 240) that redirects the light, through 90°, to exit the device where the bottom face would normally be located (step 250). It should be understood that if no mirror is extended on either the side face or the top face, the light cannot be redirected towards the bottom of the top face (step 260).

This process can be repeated in order to sequentially address exit points towards the bottom of the top face of the array (step 200). Each time the process is repeated, a pair of mirrors (one side face and one top face) is activated. Thus, by pivoting one side face mirror and one top face mirror, collimated light entering the micromirror optical multiplexer from a light source at one corner of the micromirror array can be directed to exit near normal incidence anywhere on the bottom of the top face of the micromirror array. This approach can be extended to direct light from more than one source. For example, as many as eight sources, two per corner, can be directed, provided that the side face mirrors pivoted ±45° (±15°) about their vertical centerlines and the top face mirrors pivoted ±45° (±15°) about their two orthogonal centerlines.

Figure 3:
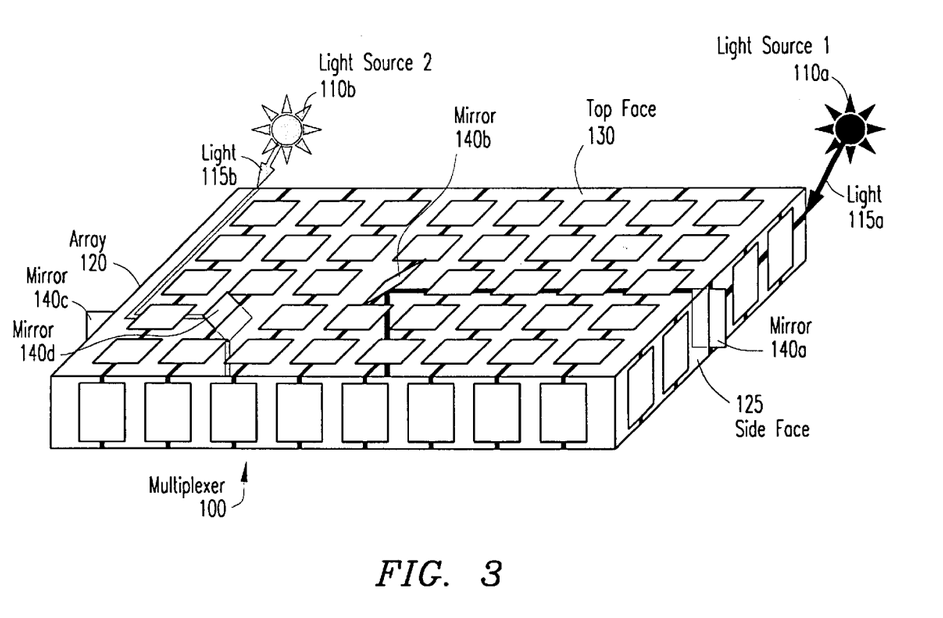
FIG. 3 is a plan view of an alternate embodiment of an exemplary micromirror optical multiplexer of the present invention.

Multiple light sources may be required, for example, when a particular sensor requires excitation at a wavelength not generated by the first light source. FIG. 3 illustrates an alternative embodiment of the micromirror optical multiplexer 100 having two separate light sources 110a and 110b. The two different excitation light sources 110a and 110b can be used to simultaneously transmit two separate beams of excitation light 115a and 115b, respectively, to illuminate two different sensors. This requires the use of four mirrors 140a–d (e.g., two side face mirrors 140a and 140c for each of the light sources 110a and 110b, respectively, and two top face mirrors 140b and 140d for the two sensors). Alternatively, the two light sources 110a and 110b can be used to illuminate the same sensor in alternation, requiring the use of three mirrors 140a–c (e.g., two side face mirrors 140a and 140c for each of the light sources 110a and 110b, respectively, and one top face mirror 140b for the sensor). In either case, the top face mirrors 140b and 140d must be able to pivot ±45° (±15°) about at least one of their centerlines.

Figure 4:
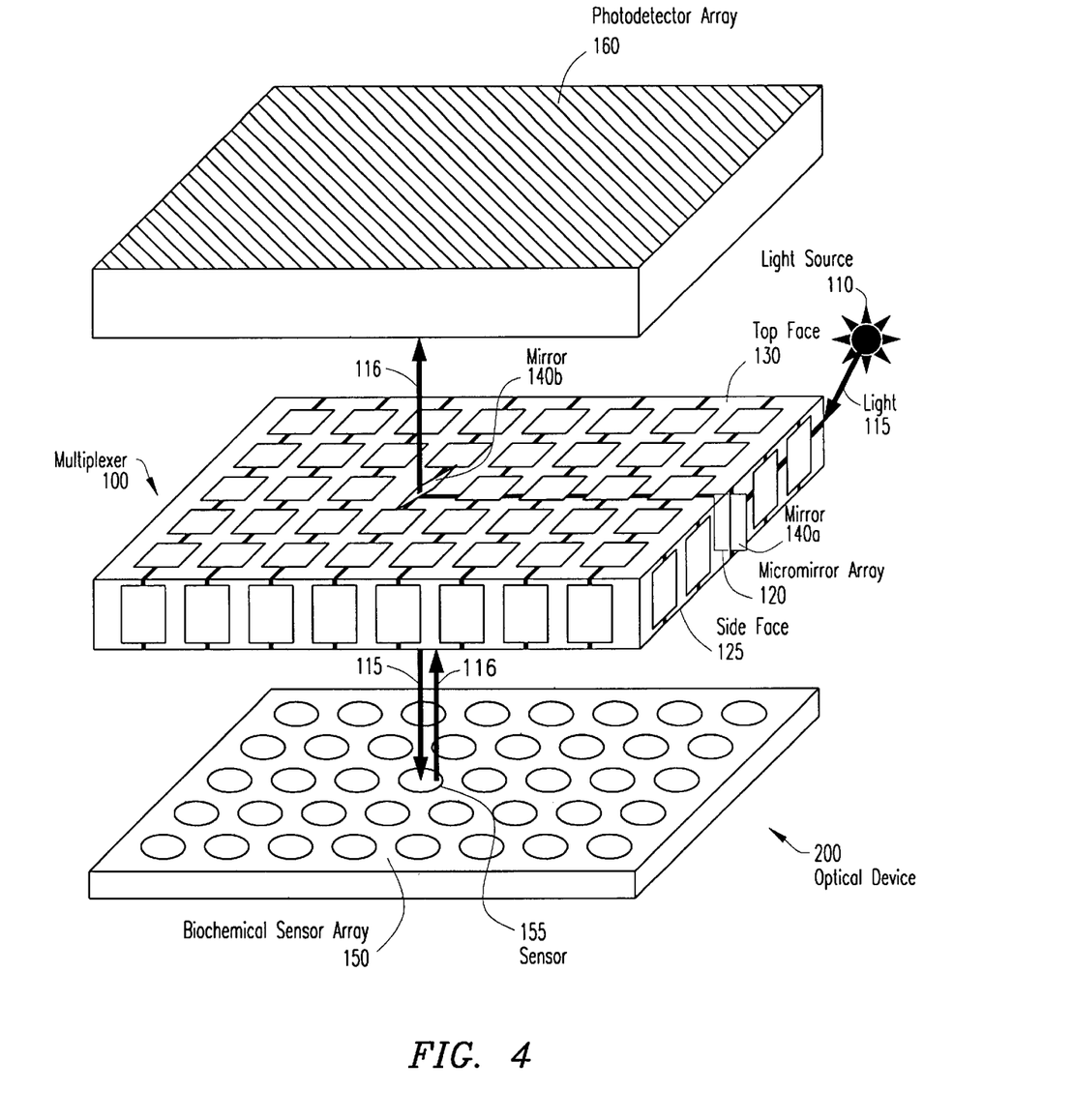
FIG. 4 is a plan view of an optical device incorporating an exemplary micromirror optical multiplexer of the present invention.

Referring now to FIG. 4, there is illustrated a portion of an optical handheld device 200 incorporating the micromirror optical multiplexer 100 described above in connection with FIGS. 1–3. The optical device 200 is capable of reading fluorescence from multiple sensors 155. Advantageously, the handheld device 200 can be made compact with a flat form factor (i.e., <10 mm thick). The optical device 200 includes the micromirror optical multiplexer 100, a photodetector array 160 and a sensor array 150 that allows single-sided illumination and detection of the sensors 155. The photodetector array 160 may be a Charge Coupled Device (CCD) imager or a Complementary Metal Oxide Semiconductor (CMOS) imager.

Although the following description assumes a biochemical sensor array 150, it should be noted that the optical device 200 may be used with any type of sensor. The optical device 200 shown in FIG. 4 has the biochemical sensor array 150 on the bottom, the micromirror multiplexer 100 in the middle and the photodetector array 160 on the top. With this construction approach, each micromirror 140b on the top face 130 must function as a dichroic filter, reflecting light 115 at the excitation wavelengths and transmitting light 116 at the emission wavelengths. Therefore, the micromirrors 140b of the top face 130 of the micromirror array 120 are preferably dichroic mirrors, which allow the illumination of a biochemical sensor 155 with excitation light 115 and the collection of the resultant fluorescent light 116 from the same side of the sensor 155.

For example, when making fluorescence measurements from a sample of blood, it is preferred that neither the excitation nor the emission light pass through the blood to avoid known autofluorescence of certain plasma proteins and scattering from the red blood cells. Therefore, one side of the sensor array 150 is in contact with the blood, allowing only the analyte of interest to diffuse into a particular sensor 155, while the other side of the sensor 155 is in contact with the micromirror array 120.

Fluorescence-based sensors 155 typically have a fluorescent compound suspended in a polymer as taught, for example, in U.S. Pat. Nos. 4,657,736, 4,892,640, 5,340,722 and 5,372,936, all of which are hereby incorporated by reference. The polymer is designed to selectively allow the analyte of interest to diffuse into the sensor 155, while excluding other analytes. The polymer also prevents the fluorophore from leaking out into the test sample (i.e., blood). The fluorophore's function is to respond to the presence of the analyte of interest by fluorescence intensity, fluorescence lifetime and/or fluorescence polarization as taught, for example, by Lakowicz in "Principles of Fluorescence Spectroscopy," 1999, which is hereby incorporated by reference. For example, ruthenium's fluorescence is quenched by the presence of oxygen. This phenomenon is used to produce oxygen sensors, glucose sensors and other metabolite sensors.

An alternative structure to the optical device 200 layers the biochemical sensor array 150, followed by the photodetector array 160, followed by the micromirror optical multiplexer 100. However, such a layered construction requires that the photodetector array 160 incorporate optically clear regions (e.g., a hole if using a silicon substrate) in alignment with each micromirror 140 above it in order to transmit the excitation light to the appropriate biochemical sensor 155. A further alternative embodiment uses conventional mirrors, not dichroic mirrors. In this embodiment, the micromirrors 140 are not transparent to emission wavelengths. Therefore, in order to transmit emission light to the photodetector array 160, the micromirrors 140b on the top face 130 of the micromirror array 120 must pivot past 45° to reflect the excitation light down to a biochemical sensor 155 adjacent to, but not directly underneath the micromirror 140b, in order to expose apertures (not shown) in the micromirror array 120 through which the emission light can pass.

Figure 5:
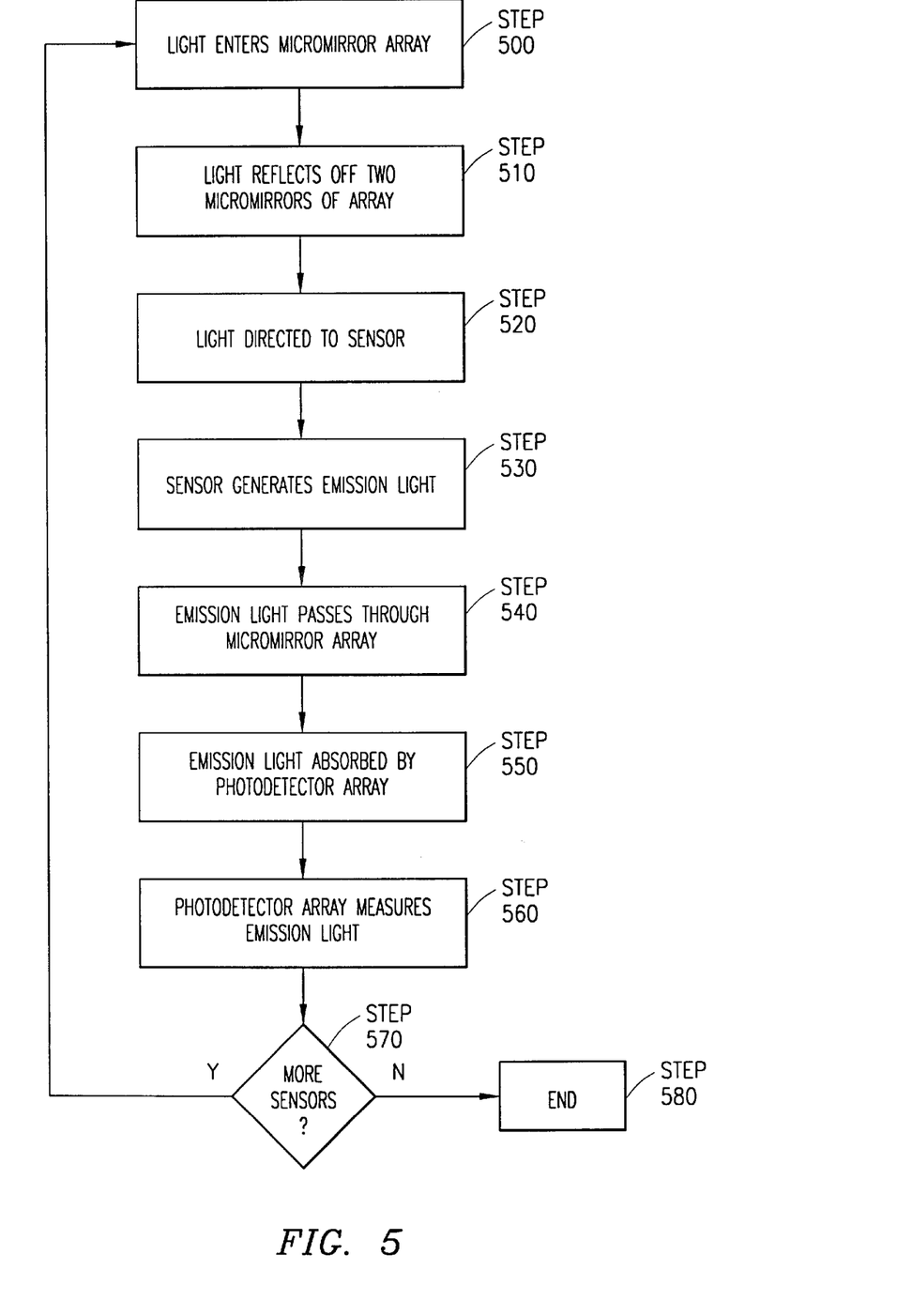
FIG. 5 is a flow chart illustrating the steps for illuminating a sensor with excitation light and collecting the resultant fluorescent light from the sensor using the optical device shown in FIG. 4.

FIG. 5 illustrates an example of the steps for utilizing the optical device of FIG. 4. In the example of FIG. 5, light (e.g., blue light) from the light source (step 500) is reflected off two micromirrors of the micromirror array (step 510) and directed to one of the fluorescence-based biochemical sensors (step 520), which generates emission light (e.g., red light) in response to the blue excitation light (step 530). The portion of the fluorescent light emitted upward, toward the top-face micromirror, passes through the top-face micromirror (rather than reflecting off of it) (step 540) and is absorbed by the photodetector array (step 550), which measures the degree of presence of the particular analyte of interest (step 560). This process can be repeated (step 570) in order to sequentially steer a focused light source to multiple sensors and read the fluorescence with a photodetector array until all of the applicable sensors have been read (step 580).

In order to pass the emission light in the example described above for FIG. 5, the top-face mirror must be appropriately coated to transmit red emission light, while reflecting blue excitation light. As discussed above, a mirror capable of reflecting at one wavelength and transmitting at another wavelength is termed a dichroic mirror. For example, assume that the top-face micromirror in FIG. 5 must reflect blue excitation light, near 450 nm, and transmit red emission light, near 610 nm. (These wavelengths are consistent with fluorescence-based biochemical sensors that use ruthenium compounds.)

Figure 6:
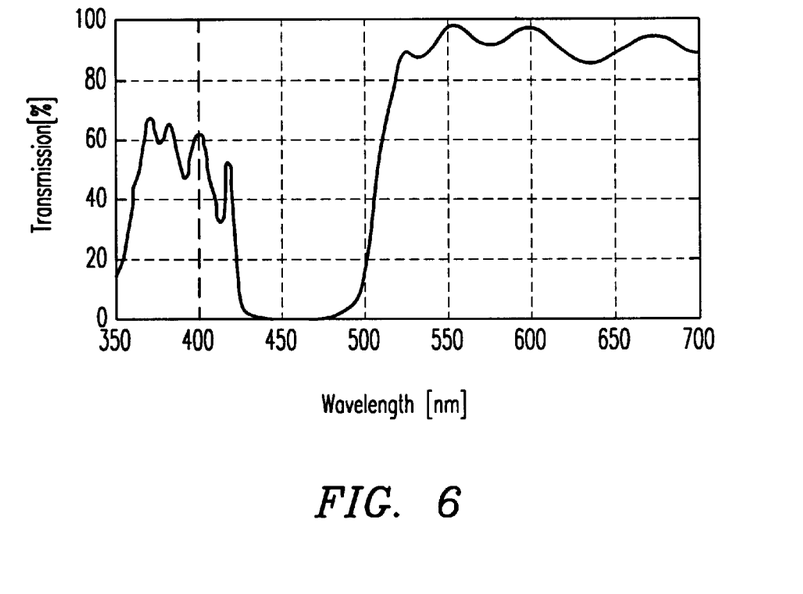
FIG. 6 is a graphical representation of the wavelength of light verses the percentage of the light transmitted through a dichroic mirror of the type used in the micromirror optical multiplexer of the present invention.

Referring now to FIG. 6, the transmission percentage of light is plotted as a function of wavelength through a particular dichroic mirror at a 45 degree incident angle. As can be seen, blue light at 450 nm has approximately zero percent transmission (i.e., one-hundred percent reflection), while wavelengths greater than 520 nm, including 610 nm, experience approximately ninety percent transmission. Therefore, a dichroic mirror having the characteristics of FIG. 6 meets the requirements of the top-face micromirror described in FIG. 5.

Figure 7:
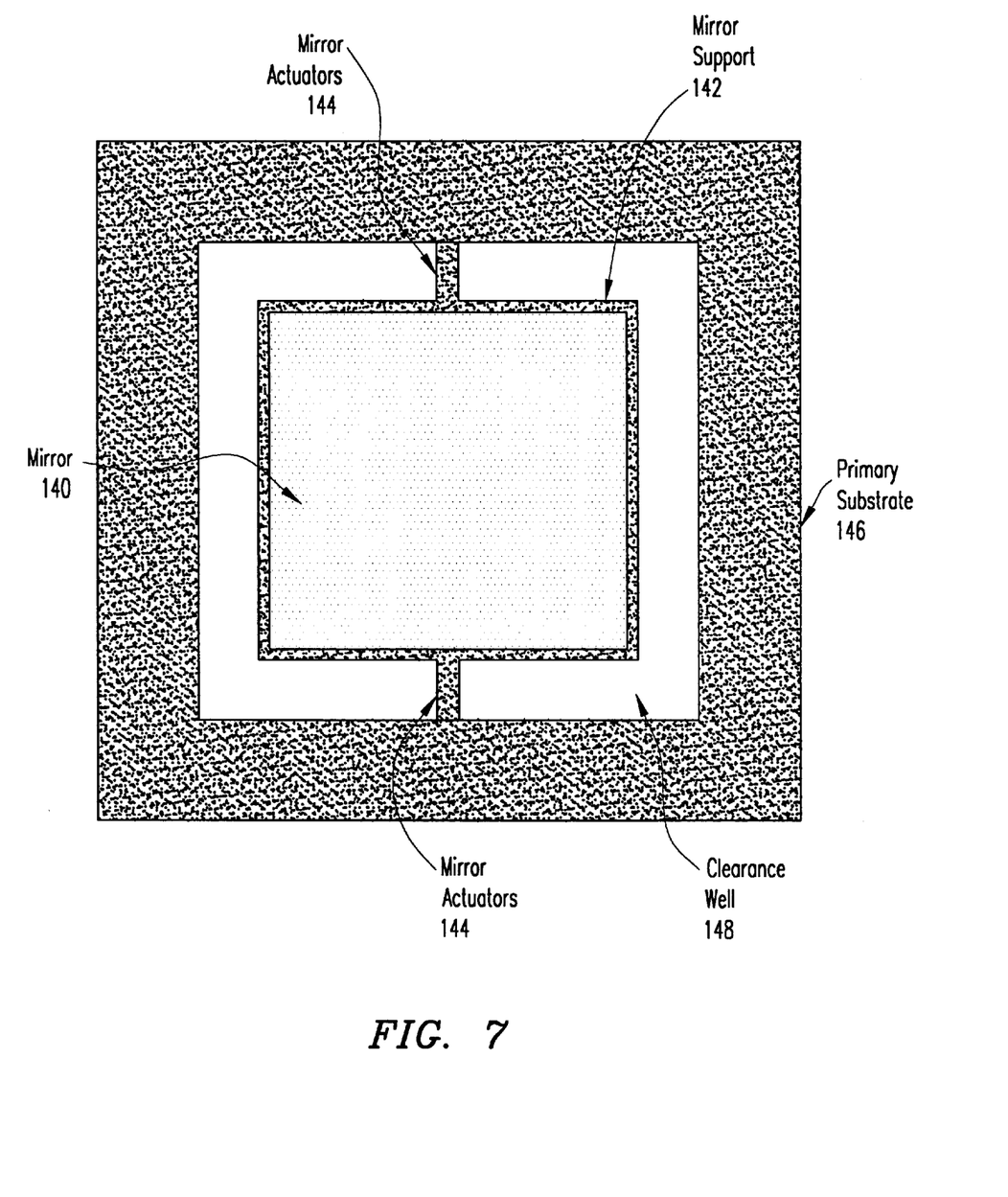
FIG. 7 is a top view of an exemplary micromirror of a micromirror array within the micromirror optical multiplexer of the present invention.
Figure 8:
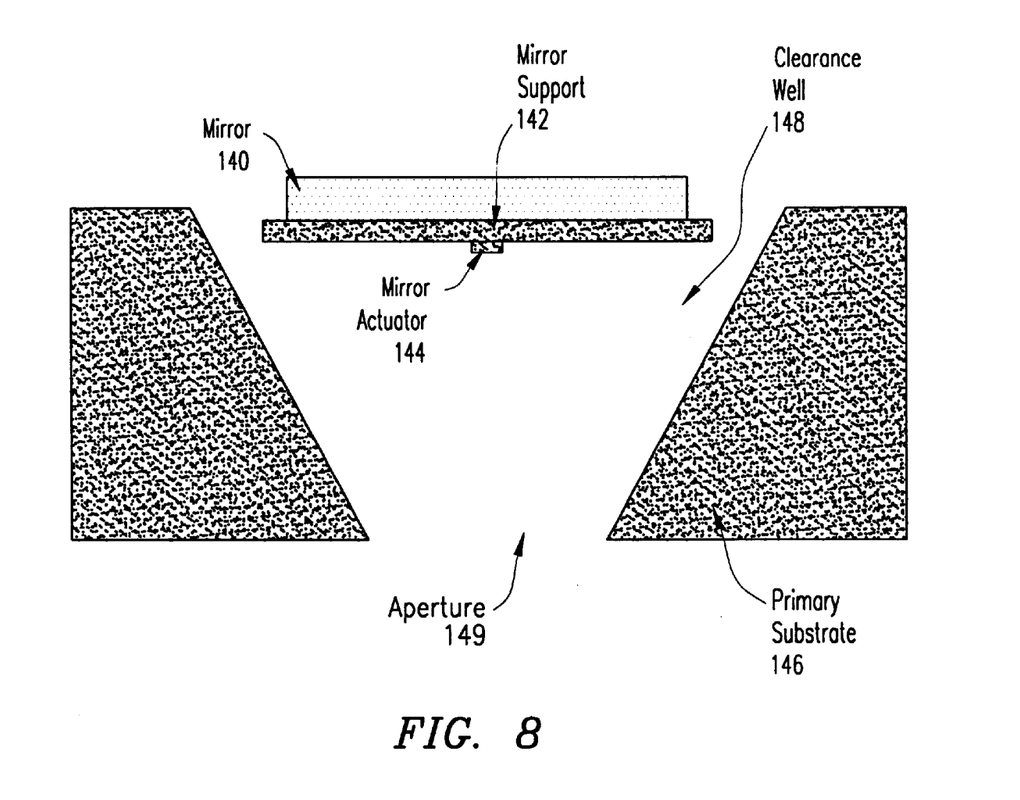
FIG. 8 is a side view of the exemplary micromirror of the micromirror array shown in FIG. 7.

Reference is now made to FIGS. 7 and 8, which show a top view and a side view, respectively, of one micromirror 140 in the micromirror array of the micromirror optical multiplexer of the present invention. The micromirror 140 itself is made of glass or quartz having an appropriate coating demonstrating specific reflection and transmission characteristics, as described above. A mirror support 142 surrounds the micromirror 140 and connects to a primary substrate 146 via mirror actuators 144. The mirror support 142 and mirror actuators 144 are preferably made up of silicon. The mirror actuators 144 pivot the micromirror 140 by 45° about a centerline of the micromirror 140 located between the two actuators 144. It should be understood that the actuators 144 may pivot the micromirror 140 in only one direction or in both directions, depending on the number of light sources. It should further be understood that additional actuators (not shown) perpendicular to the actuators 144 shown may be included to pivot the micromirror 140 by ±45° about its two orthogonal centerlines. A clearance well 148 in the primary substrate 146 gives the clearance between the primary substrate 146, which is stationary, and the moving mirror support 142 and mirror 140.

The primary substrate 146 further contains microelectromechanical (MEM) devices responsible for activating the actuators 144. Preferably, the primary substrate 146 is silicon and the MEM devices are constructed using conventional semiconductor processing techniques. However, silicon is not transparent to visible light, as is required for the mirror 140 and regions of the primary substrate 146 directly below the mirror. Therefore, in one embodiment, the primary substrate 146 is formed with the well 148 extending completely through the primary substrate 146 to form an aperture 149 for the free passage of visible light.

In an alternative embodiment, the mirror actuators 144 can serve merely as torsion bars to restore the mirror 140 to a neutral position after a driving force has been removed. In this embodiment, the driving force may be an electromagnetic actuator or electrostatic actuator (not shown) residing below the mirror support 142 that attracts or repels the mirror 140.

As will be recognized by those skilled in the art, the innovative concepts described in the present application can be modified and varied over a wide range of applications. Accordingly, the scope of patented subject matter should not be limited to any of the specific exemplary teachings discussed, but is instead defined by the following claims.

We claim:

1. A micromirror array for use within an optical multiplexer, comprising:
   a top face having a plurality of pivotable micromirrors thereon; and
   at least one side face having a plurality of pivotable micromirrors thereon, a first one of said pivotable micromirrors on said at least one side face being capable of redirecting a beam of light propagating substantially parallel to said at least one side face towards said top face to propagate substantially parallel to said top face, a second one of said pivotable micromirrors on said top face being capable of redirecting the beam of light propagating substantially parallel to said top face to exit said micromirror array.

2. The micromirror array of claim 1, wherein said first pivotable micromirror is capable of redirecting the beam of light, through 90°, along said top face, and said second pivotable micromirror is capable of redirecting the beam of light, through 90°, to exit said micromirror array near normal incidence on the bottom of said top face of said micromirror array.

3. The micromirror array of claim 2, wherein said first pivotable micromirror has orthogonal vertical and horizontal centerlines extending between sides of said first pivotable micromirror, said horizontal centerline being substantially parallel to the propagation direction of the beam of light along said side face, said first pivotable micromirror being adapted to be pivoted 45 degrees about said vertical centerline towards the beam of light to redirect the beam of light through 90° along said top face.

4. The micromirror array of claim 3, wherein said second pivotable micromirror has orthogonal vertical and horizontal centerlines extending between sides of said second pivotable micromirror, said horizontal centerline being substantially parallel to the propagation direction of the beam of light along said top face, said second pivotable micromirror being adapted to be pivoted 45 degrees about said vertical centerline towards the beam of light to redirect the beam of light to exit said micromirror array.

5. The micromirror array of claim 1, wherein said first and second pivotable micromirrors are adapted to be pivoted about an edge of said respective first and second pivotable micromirrors to redirect the beam of light.

6. The micromirror array of claim 1, wherein each said micromirror of said micromirror array comprises:
   a mirror;
   a mirror support surrounding said mirror;
   mirror actuators connected to at least two sides of said mirror support; and
   a primary substrate connected to said mirror actuators and having circuitry therein for activating said mirror actuators to pivot said mirror.

7. The micromirror array of claim 6, wherein said primary substrate, said mirror support and said mirror actuators are constructed of silicon, said primary substrate further including an aperture therein under said mirror for the passage of visible light.

8. The micromirror array of claim 1, wherein each said micromirror along said top face of said micromirror array is a dichroic mirror.

9. A micromirror optical multiplexer, comprising:
   a micromirror array having at least one side face and a top face, said micromirror array further having pivotable micromirrors on said at least one side face and said top face, said micromirror array being capable of receiving a beam of light near one of the corners of said micromirror array to propagate substantially parallel to a first one of said at least one side face, a first one of said pivotable micromirrors on said first side face being capable of redirecting the beam of light towards said top face to propagate substantially parallel to said top face, a second one of said pivotable micrormirrors on said top face being capable of redirecting the beam of light propagating substantially parallel to said top face to exit said micromirror array.

10. The multiplexer of claim 9, wherein said first pivotable micromirror is capable of redirecting the beam of light, through 90°, along said top face, and said second pivotable micromirror is capable of redirecting the beam of light, through 90°, to exit said micromirror array near normal incidence on the bottom of said top face of said micromirror array.

11. The multiplexer of claim 10, wherein said first pivotable micromirror has orthogonal vertical and horizontal centerlines extending between sides of said first pivotable micromirror, said horizontal centerline being substantially parallel to the propagation direction of the beam of light along said first side face, said first pivotable micromirror being adapted to be pivoted 45 degrees about said vertical centerline towards the beam of light to redirect the beam of light through 90° along said top face.

12. The multiplexer of claim 11, wherein said second pivotable micromirror has orthogonal vertical and horizontal centerlines extending between sides of said second pivotable micromirror, said horizontal centerline being substantially parallel to the propagation direction of the beam of light along said top face, said second pivotable micromirror being adapted to be pivoted 45 degrees about said vertical centerline towards the beam of light to redirect the beam of light to exit said micromirror array.

13. The multiplexer of claim 1, further comprising:
   at least two light sources for providing respective beams of light along respective side faces of said micromirror array.

14. The multiplexer of claim 13, wherein said first and second pivotable micromirrors are further capable of simultaneously redirecting each of the beams of light towards a different respective sensor.

15. The multiplexer of claim 13, wherein said first and second pivotable micromirrors are further capable of sequentially directing the beams of light towards a single sensor.

16. An optical handheld device for reading fluorescence from at least one sensor, said device comprising:
   a micromirror optical multiplexer having a micromirror array being adapted to receive a beam of light near a corner of said micromirror array, the beam of light propagating substantially parallel to one of four side faces of said micromirror array until the beam of light reaches a first pivotable micromirror on said side face of said micromirror array, said first pivotable micromirror being adapted to be pivoted to redirect the beam of light to propagate substantially parallel to said top face of said micromirror array towards a second pivotable micromirror on said top face of said micromirror array, said second pivotable micromirror being adapted to be pivoted to redirect the beam of light to exit said micromirror array near normal incidence on the bottom of said top face of said micromirror array;
   a sensor array having a sensor under said second pivotable micromirror for receiving said beam of light and emitting fluorescence in response to said received beam of light; and
   a photodetector array for receiving said emitted fluorescence from said sensor and measuring said emitted fluorescence.

17. The device of claim 16, wherein said photodetector array is above said top face of said micromirror array.

18. The device of claim 17, wherein said second pivotable micromirror is a dichroic mirror to reflect said beam of light towards said sensor and to transmit said emitted fluorescence from said sensor to said photodetector array.

19. The device of claim 16, wherein said photodetector array is between said micromirror array and said sensor array, said photodetector array having holes therein for transmitting said beam of light from said second pivotable micromirror to said sensor.

20. A method for directing at least one beam of light towards at least one sensor, said method comprising:
   directing said beam of light towards a corner of a micromirror array having a plurality of micromirrors on at least one side face and a top face;
   propagating said beam of light substantially parallel to a first one of said at least one side face;
   pivoting a first pivotable one of said micromirrors on said first side face to redirect said beam of light to propagate said beam of light substantially parallel to said top face; and pivoting a second pivotable one of said micromirrors on said top face to redirect said beam of light to exit said micromirror array near normal incidence on the bottom of said top face of said micromirror array.

21. The method of claim 20, wherein said first pivotable micromirror has orthogonal vertical and horizontal centerlines extending between sides of said first pivotable micromirror, said horizontal centerline being substantially parallel to the propagation direction of said beam of light along said first side face, said step of pivoting said first pivotable micromirror further comprising:

pivoting said first pivotable micromirror 45 degrees about said vertical centerline towards said propagating beam of light to redirect said beam of light through 90° along said top face.

22. The method of claim 21, wherein said second pivotable micromirror has orthogonal vertical and horizontal centerlines extending between sides of said second pivotable micromirror, said horizontal centerline being substantially parallel to the propagation direction of said beam of light along said top face, said step of pivoting said second pivotable micromirror further comprising:

pivoting said second pivotable micromirror 45 degrees about said vertical centerline towards said propagating beam of light to redirect said beam of light to exit said micromirror array.

23. The method of claim 20, wherein said step of directing further comprises:

directing at least two beams of light towards respective corners of said micromirror array, said step of propagating further comprising:

propagating said at least two beams of light along respective side faces of said micromirror array.

24. The method of claim 23, further comprising:

directing each said beam of light simultaneously towards a different respective one of said at least one sensor using respective said first and second pivotable micromirrors of said micromirror array.

25. The method of claim 23, further comprising:

directing each said beam of light sequentially towards a single one of said at least one sensor using respective said first pivotable micromirrors of said micromirror array and said second pivotable micromirror of said micromirror array.

26. The method of claim 20, further comprising:

transmitting emitted light from said at least one sensor through said second pivotable micromirror.

* * * * *